United States Patent
Gurzadyan et al.

(10) Patent No.: US 10,068,050 B2
(45) Date of Patent: Sep. 4, 2018

(54) REVEALING SOMATIC SEQUENCES IN HUMAN GENOME VIA KOLMOGOROV-ARNOLD TECHNIQUE

(71) Applicants: Vahagn Gurzadyan, Yerevan (AM); Branislav Vlahovic, Chapel Hill, NC (US)

(72) Inventors: Vahagn Gurzadyan, Yerevan (AM); Branislav Vlahovic, Chapel Hill, NC (US)

(*) Notice: Subject to any disclaimer, the term of this patent is extended or adjusted under 35 U.S.C. 154(b) by 259 days.

(21) Appl. No.: 14/067,102

(22) Filed: Oct. 30, 2013

(65) Prior Publication Data
US 2015/0154346 A1 Jun. 4, 2015

(51) Int. Cl.
*G06F 19/18* (2011.01)

(52) U.S. Cl.
CPC .................................. *G06F 19/18* (2013.01)

(58) Field of Classification Search
None
See application file for complete search history.

(56) References Cited

U.S. PATENT DOCUMENTS

| | | | |
|---|---|---|---|
| 6,291,182 B1 * | 9/2001 | Schork et al. | 435/6 |
| 7,809,765 B2 * | 10/2010 | Evans et al. | 707/802 |
| 8,560,469 B2 * | 10/2013 | Laine | 706/12 |

OTHER PUBLICATIONS

Gurzadyan VG, et al, Detecting somatic mutations in genomic sequences by means of Kolmogorov-Arnold analysis. Royal Society Open Science 2, (2015) 150143.*
V. G. Gurzadyan and A.A. Kocharyan, Kolmogorov stochasticity parameter measuring the randomness in Cosmic Microwave Background, Astronomy and Astrophysics, (2008) AA1.*
Arnold VI, To what extent are arithmetic progressions of fractional parts stochastic? Russian, Math. Surveys 63, (2008) 205-220.*
Arnold VI, Stochastic and deterministic characteristics of orbits in chaotically looking dynamical systems. Trans. Moscow Math. Soc. 70, (2009) 31-69.*

* cited by examiner

*Primary Examiner* — Joseph Woitach (57) ABSTRACT

Kolmogorov-Arnold analysis is invented as a tool for the study of tumor and normal coding in human genomics sequencing to identify tumor-specific (somatic) sequences and copy number alterations. The technique enables to reveal quantitatively somatic sequences in the dataset of the genomic DNA purified from tumor and normal specimens. The computer power requirements for an analysis are modest ones.

10 Claims, 5 Drawing Sheets

Specification includes a Sequence Listing.

SEQUENCE LISTING

<160> NUMBER OF SEQ ID NOS: 18

<210> SEQ ID NO 1
<211> LENGTH: 2100
<212> TYPE: DNA
<213> ORGANISM: Homo sapiens
<220> FEATURE:
<221> NAME/KEY: misc_feature
<222> LOCATION: (1001)..(1005)
<223> OTHER INFORMATION: n is a, c, g, or t
<220> FEATURE:
<221> NAME/KEY: misc_feature
<222> LOCATION: (1053)..(1053)

<223> OTHER INFORMATION: n is a, c, g, or t
<220> FEATURE:
<221> NAME/KEY: misc_feature
<222> LOCATION: (1073)..(1073)
<223> OTHER INFORMATION: n is a, c, g, or t

<400> SEQUENCE: 1

```
acagagctga gtcacgtggt ggaataaata caagtgtgtt ggctcaagcc cagagttgct      60
gatagggaga tggatgcctc ctgccccatg ggctgtaaac tgcctggaac atgaccctcc     120
tagaccaact ccacactgga cttcatcagc aactgcaaca cctggagacc tgcttgctgc     180
aggtagtggg agaaggagaa gctcagagga gtgggaatgg ggtgggtctt cctgggcatg     240
gccaggctgt gccccagcct aggggcttgg tgtggtggtg ttggccaggc ttggcaggca     300
tagtaactct gatatgcagt tgggtaattt aaaaattgta gtttaagtgg tttctgcacg     360
aatctagatt ctctaaatga aatctaactc agctcccata ttccactgct taaactgagc     420
acaggacgtg cacttggata gtaaaccagg tgtctcctca aagccctaat atattcagca     480
tctctatcaa aggcgccttt gagaaagact taagcatgat gccccccgc actgactttc      540
atgtggcagc caagcaagcg ccggactcct caagggctgg caggagagca acaggagatg     600
ttccagcctt gggcatagtc agggactctc gtgggacccc ccgagtagaa acacagatgt     660
gtctccctgg gtccctgcca ggtcccctct cagcctggat ccattgaaac caatgctatg     720
cataccactc ctccttccaa ggctgtcatc ttgcagtctg cctctgtctc caagaagtac     780
ctcccatttt acctggggct cccgagcctc tcctcgtggg aaggcgaca cacagcagcc      840
gtgaaggtgg ctgccgagaa gttgcccagg ctgcttccaa acccacggc ctgctccacg      900
gttttgaaca tttggcaatg tgtattagca cagctcttcc ctttagcaag atttgttttg     960
cggttccaga taggtcattt ccaggcctca ttccgccaag nnnnnggtta accaaggaaa    1020
aaaacttaaa aggcatcatt gtaaacatca agntgatttg cagaagttga atnattgatt    1080
tgaaagtttt aattttgtaa ttctctattt tcctagttat atatgctatc atatgtctgt    1140
ttttctcctc ttgaagtttc cctgaaacct gggctcttga agacgcatca ctggagcaga    1200
cctcagagat gttgaccca gctgggacat cagtaccaca cgccacaaaa tccccatgtc     1260
aatagcacca ccccttccct ctgctggagg atacaatccc agccccacag agggatccct    1320
tactactgga atgcagacac agacgttgga tcctggttct ccccagatga caccaactcc    1380
gtggttacca aataggcaaa cccttcctct gtcagtactg ctgtgaacag acctgcgtgg    1440
ctggtcctgt gtttgggtaa aacattaaat gacaactta attgaaaaaa cctggggaag     1500
gccagaacac tgattggtgg ataccctcgt cttcagtctc tctggagtcc tttcacttcc    1560
attgccttcg ggacagggaa cacctcctcc cccacccctca ccccagggag ggcaacgttc    1620
attctgctgt ggcaatgggc cttggggat aggagttgga tatctgcgta agggaggaca     1680
ggtggaaagt gatatggaac gtgcgtaaaa tgacaagtca aggaacgaca ggaagcaggg    1740
aaagtcgaca cactgcaaga aaaatagtga taatgctaaa taaaaaaccg tcatgagaaa    1800
catgcacccc aactaagctc aggtcctgcg tagattttg tgggaatcag cttccaagga     1860
ctaggtcatt tattgccct gtgttcctag gtcagcggtg gaggtatggt caacctatag     1920
taagttagta aatgataagg ggaggaagaa atggaaacct aaacatctac tgcaatgaaa    1980
accaacagca atatcaggag agaacaaaca aaactatagt gctggacaca agtggaaagt    2040
atattccttt cattaaaatt atcttcctga catgcagtga ggaaattgtg tttccaagaa    2100
```

```
<210> SEQ ID NO 2
<211> LENGTH: 2200
<212> TYPE: DNA
<213> ORGANISM: Homo sapiens
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (1018)..(1020)
<223> OTHER INFORMATION: n is a, c, g, or t
<220> FEATURE:
<221> NAME/KEY: misc_feature
<222> LOCATION: (1022)..(1022)
<223> OTHER INFORMATION: n is a, c, g, or t
<220> FEATURE:
<221> NAME/KEY: misc_feature
<222> LOCATION: (1039)..(1039)
<223> OTHER INFORMATION: n is a, c, g, or t

<400> SEQUENCE: 2
```

| | | | | | |
|---|---|---|---|---|---|
| cccaagctgg | aatgcagtgg | ctgttcacag | atgcagtcat | agcactgtag | agcatcaggt | 60 |
| gttcctccca | tggcaggagg | gaagaaaccc | agcaaacgtc | aatgaaagtc | aaatgaaatc | 120 |
| tttagatgtc | cttccatatt | ttatggtgac | gatctgcatc | atgggtccgg | cgggtccggc | 180 |
| ccaggcagcc | tctggagcaa | aaatgggata | cagaaaaaga | cagaacatca | tagttctaag | 240 |
| ttactgattt | ggagtttcac | tcttgttgct | gagactggag | tgcaatgacg | cgatctcggc | 300 |
| gactcactgg | aggaatgtgc | catcacttgt | tcaaatagcc | acggcccttg | agtgaagagg | 360 |
| ctggggatga | cactaccact | gtactgttct | ggcatgctct | ttttttcctt | tctttccttt | 420 |
| agaagaagta | gatgaacgag | acgatgcagc | tctgccattc | aaggctctaa | tgttcctaac | 480 |
| cctgatgagg | ccgtccctag | tggcatcact | gaggcactgt | acggtccttg | caatgtcaaa | 540 |
| cttactcaat | agttntctga | ttgcttcccc | ttccataggt | tgtgggaata | attgagtcac | 600 |
| ccaagaaggc | cttgaccttt | ccagcaagtg | ggaaggtata | atcagtctcc | tagagcagga | 660 |
| ctcacctgtt | ttaactccac | ctcccgcccc | aaccccagtg | gagatcattc | gcataaaggg | 720 |
| cctgggccac | tgaacgggct | aagcaaatat | gaattatttg | gatcggttgg | cagaagaggt | 780 |
| caatgataaa | ttgcaagaaa | actctacttt | gaggacagtc | cggctctcaa | ggagcacgtc | 840 |
| ttccacaacc | tgatctctct | ttctttaccc | tacatccaag | ggcttgaaca | tttcttgact | 900 |
| gcctttggga | gaccctcttc | agatgactgc | catcaaaaga | gtcatagaaa | gctgtgcagg | 960 |
| gcatcccaga | caggggttgg | gcctccctga | tggacaagga | cgcctcccta | ttcctctnnn | 1020 |
| ancaggtctc | aaggtgagna | cgttaagcct | tccctcaccc | cctcacagtg | gtgcagttct | 1080 |
| cggcctctcg | gcctggcttc | tctatgtatg | tcacatgcac | ttgcttaact | ctaggcatga | 1140 |
| agaacttctc | gaatgaatac | agagttcctg | aactgaatgt | tcaaaatgga | gtgttaaaat | 1200 |
| acttctaatt | ttttctaac | aggctccaca | atctctcata | tatgtttttt | tgttatgttg | 1260 |
| acactgaagt | ggaaatgaaa | gaaatctata | caagtaacca | gaggaagaac | ctgcaggagc | 1320 |
| catccctgac | ttgctttgac | caagcccaag | gtttaaaagt | ttgtcccaga | cctccagtta | 1380 |
| taatgcttct | atgcagatt | tagattctgc | tgcagttgtt | cttctttttg | tataaataat | 1440 |
| cttctttgtt | tgggcacacc | agctgttgcc | ttctggtggg | tggggctggg | tggagccacc | 1500 |
| tttagacgtt | ctacatcaat | agctcccaat | ttgaggtact | tgggctgctt | tcctgacagc | 1560 |
| ttggggtttg | agaccctgga | aaactgcagg | aaggtaccgt | gattcaggtg | catttgtttc | 1620 |
| aagccttgag | gtttcatggg | gcaaatgatg | ttgaagttta | agaatatcaa | cgttttatat | 1680 |

-continued

```
ggtattgtgt ttttaggaac tctcctgtat gagttgtctg atgttgagta aggcatgaac    1740
tacggttaaa atgcccaaca cctggcttgc ccaccctcct gtcccctgcc ccttcctggt    1800
acacacaatt gtatagattg ccagctttt  tataaactgg aaatttcttg aaatcatcct    1860
accaaaaaga catacatgct cgcatgttca ccacaatact tatgtccccc aataaactgt    1920
aagcttcagg gggaatgagt gaatgaccag tgttctaagt agaatcttaa tcttggattg    1980
ttaactcaat gaattctcat atgtggtccc tgggcttctc cattcaccag cccccaatca    2040
tttcttcctg tacaaggaat gaaacagtca ttgaggtcac ctctagcaag tctcccagca    2100
gatagctacc actttccaca tcacagtagt aataaattaa atcataatat acttaatatt    2160
aggtgtactt tttaaaacta aattttaaaa gaaaaaggag                          2200
```

<210> SEQ ID NO 3
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 3
gagccnaaga c                                                          11

<210> SEQ ID NO 4
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 4
aggccngccc t                                                          11

<210> SEQ ID NO 5
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 5
gatctnaaaa a                                                          11

<210> SEQ ID NO 6
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 6
gtgagnacgt t                                                          11

<210> SEQ ID NO 7
<211> LENGTH: 11
<212> TYPE: DNA
<213> ORGANISM: Homo sapiens

-continued

```
<220> FEATURE:
<221> NAME/KEY: misc_feature
<222> LOCATION: (6)..(6)
<223> OTHER INFORMATION: n is a, c, g, or t

<400> SEQUENCE: 7
gtgacncata g                                                            11

<210> SEQ ID NO 8
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 8
tgcctntgga t                                                            11

<210> SEQ ID NO 9
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 9
tcatgnctgt g                                                            11

<210> SEQ ID NO 10
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 10
tcaagntgat t                                                            11

<210> SEQ ID NO 11
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 11
aaaganaaat t                                                            11

<210> SEQ ID NO 12
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 12
catctnaaaa a                                                            11
```

<210> SEQ ID NO 13
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 13
agaagnaaaa a                                                          11

<210> SEQ ID NO 14
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 14
attttntctt t                                                          11

<210> SEQ ID NO 15
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 15
tgcccnggct g                                                          11

<210> SEQ ID NO 16
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 16
ctttcntttc t                                                          11

<210> SEQ ID NO 17
<211> LENGTH: 11
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 17
tcttcntttt t                                                          11

<210> SEQ ID NO 18
<211> LENGTH: 300
<212> TYPE: DNA
<213> ORGANISM: Homo sapiens

<400> SEQUENCE: 18
tatgtccccc aataaactgt aagcttcagg gggaatgagt gaatgaccag tgttctaagt      60

```
agaatcttaa tcttggattg ttaactcaat gaattctcat atgtggtccc tgggcttctc    120
cattcaccag cccccaatca tttcttcctg tacaaggaat gaaacagtca ttgaggtcac    180
ctctagcaag tctcccagca gatagctacc actttccaca tcacagtagt aataaattaa    240
atcataatat acttaatatt aggtgtactt tttaaaacta aattttaaaa gaaaaaggag    300
```

REVEALING SOMATIC SEQUENCES IN HUMAN GENOME VIA KOLMOGOROV-ARNOLD TECHNIQUE

The sequence listing is included as a computer fie on the compact disc filed on Arp. 20, 2018 referenced as AN_14067102_ST25.txt Copy1, Copy2, and Copy 3. The file is created on Jul. 26, 2016 by Patent-In version 3.5 and has size of 11 kb.

SUMMARY OF THE INVENTION

The Kolmogorov-Arnold technique is invented for the analysis of the statistical properties of the human genome and revealing the somatic sequences. This technique has been developed by Arnold during 2008-2009 based on the work of Kolmogorov of 1933, when he (Arnold) demonstrated its power on diverse examples of dynamical systems and number theory. The carried out applications for physical problems reveal the efficiency of the technique to separate signals with given correlations from composite signals, enabling to detect weak subsignals due to their correlation properties. The technique has been applied to astrophysical problems, i.e. for the analysis of observational datasets, e.g. on the cosmic microwave background radiation obtained by the Wilkinson Microwave Anisotropy Probe's (NASA), X-ray galaxy cluster data obtained by XMM-Newton satellite. The technique had enabled e.g. not only to reveal cosmic sources found by several other methods but also to predict others, then unknown, soon after discovered by the Fermi satellite. Recently this technique was instrumental for detection of the Yarkovsky-Rubincam (thermal thrust) effect for LAGEOS satellites during the study of Lense-Thirring effect predicted by General Relativity. The application to the human genome datasets enables to trace the somatic (tumor) sequences within the normal environment sequences. The application steps include: (a) modeling and extensive numerical experiments with sequences of the characteristics of the human genomic sequence: the revealing of the behavior of the stochastic parameter; (b) development of the criteria for the separation of particular signals, study of the sensitivity to the input parameters and the classes of those generated signals, estimation of their degree of randomness; (c) study of the systems with non-Gaussian cumulative functions; (d) the work with real genomic sequences. The analysis of a single genome sequence requires modest computer power.

OTHER PUBLICATIONS

Stephen J. C., Statistical methods of DNA sequence analysis: detection of intragenic recombination or gene conversion, Mol. Biol. Evol. 2(6):539-556. 1985, Burge, C. and Karlin, S. "Prediction of complete gene structures in human genomic DNA." J. Mol. Biol. 268, 78-94, 1997.

Long A D, Mangalam H J, Chan B Y, Tolleri L, Hatfield G W, et al. (2001) Improved statistical inference from DNA microarray data using analysis of variance and a Bayesian statistical framework. Analysis of global gene expression in *Escherichia coli* K12. J Biol Chem 276: 19937-19944;

Zhang M. Q., Computational prediction of eukaryotic protein-coding genes. Nature Reviews Genetics 3, 698-709, 2002;

Smyth G K (2004) Linear models and empirical bayes methods for assessing differential expression in microarray experiments. Stat. Appl. Genet. Mol. Biol. 3;

Daruwala, R. S., Rudra, A., Ostrer, H., Lucito, R., Wigler, M., Mishra, B. (2004) A versatile statistical analysis algorithm to detect genome copy number variation. Proc. Natl. Acad. Sci. 101:16292-16297

Smyth G. K.: Limma: linear models for microarray data. In Bioinformatics and Computational Biology Solutions using R and Bioconductor. Edited by Gentleman R, Carey V, Dudoit S, Irizarry R, Huber W. New York: Springer; 2005:397-420;

Rakyan V K, Down T A, Thorne N P, Flicek P, Kulesha E, Gräf S, Tomazou E M, Backdahl L, Johnson N, Herberth M, Howe K L, Jackson D K, Miretti M M, Fiegler H, Marioni J C, Birney E, Hubbard T J P, Carter N P, Tavaré S, Beck S: An integrated resource for genome-wide identification and analysis of human tissue-specific differentially methylated regions (tDMRs), Genome *Res* 2008, 18:1518-1529;

Ruike Y, Imanaka Y, Sato F, Shimizu K, Tsujimoto G: Genome-wide analysis of aberrant methylation in human breast cancer cells using methyl-DNA immuno precipitation combined with high-throughput sequencing, BMC Genomics 2010, 11:137;

Jeong Y-S, Kim D, Lee Y S, Kim H-J, Han J-Y, et al. Integrated Expression Profiling and Genome-Wide Analysis of ChREBP Targets Reveals the Dual Role for ChREBP in Glucose-Regulated Gene Expression. PLoS ONE 6(7) (2011);

Langmead B, Trapnell C, Pop M, Salzberg S L (2009) Ultrafast and memory-efficient alignment of short DNA sequences to the human genome. Genome Biol 10: R25; vol. 110 no. 19 J. A., et al Imprinted expression of genes and small RNA is associated with localized hypomethylation of the maternal genome in rice endosperm PNAS May 7, 2013, 110 no. 19 7934-7939;

Ewens W. J., Grant G., Statistical Methods In Bioinformatics: Springer Verlag, 2005;

Deonier R. C., Waterman M. S., Tavare S., Computational Genome Analysis: An Introduction, Springer Verlag, 2005;

Balding D. J., Bishop M., Cannings C., Weight Array Method, Handbook of Statistical Genetics Wiley, 2008.

Huang S, Yeo A A, Li S D., Modification of Kolmogorov-Smirnov test for DNA content data analysis through distribution alignment, Assay Drug Dev. Technol. 2007, 5, 663.

Hodgson D. R., Wellings R, Orr M. C., McCormack R., Malone M., et al. Circulating tumor-derived predictive biomarkers in oncology, Drug Discov. Today 15: 98-101 (2010);

Hicks J. et al, Novel patterns of genome rearrangement and their association with survival in breast cancer, *Genome Res.* 2006.16: 1465-1479;

Closas P., Coma E., and Méndez L., Sequential detection of influenza epidemics by the Kolmogorov-Smirnov test, BMC Med. Inform. Decis. Mak. 12 (2012), 112;

Chen, Z., Liu, Q. & Nadarajah, S. A new statistical approach to detecting differentially methylated loci for case control Illumina array methylation data. Bioinformatics 28, 1109-13 (2012);

Hansen, K. D. et al. Increased methylation variation in epigenetic domains across cancer types. Nat Genet. 43, 768-75 (2011).

Du X., Wojtowicz D., Bowers A., Levens D., Benham T. C., Przytycka M., The genome-wide distribution of non-B DNA motifs is shaped by operon structure and suggests the transcriptional importance of non-B DNA structures in *Escherichia coli*, Nucl. Acids Res. (2013);

Orlov Y. L., Potapov V. N., Complexity: an internet resource for analysis of DNA sequence complexity, Nucleic Acids Res. (2004) Jul. 1; 32: W628-W633;

Ming. Li, P. M. B. Vitanyi, An introduction to Kolmogorov complexity and its applications, Springer-Verlag, 2008, p. 664;

Bin Li, Yi-Bing Li and Hong-Bo He, LZ Complexity Distance of DNA Sequences and Its Application in Phylogenetic Tree Reconstruction, Geno. Prot. Bioinfo, 3, 206 (2005).

U.S. Pat. No. 8,560,469 B2 (2013), Laine; Unto (Vantaa, FI), Rasanen; Okko (Kauniainen, FI), Method for a pattern discovery and recognition.

U.S. Pat. No. 7,809,765 B2 (2010), Evans; Scott Charles (Schenectady, N.Y.), Markham; Thomas Stephen (Schenectady, N.Y.), Torres; Andrew Soliz (Troy, N.Y.), Sequence identification and analysis.

U.S. Pat. No. 6,291,182 B1 (2001), Schork, et al., Methods, software and apparati for identifying genomic regions harboring a gene associated with a detectable trait.

BACKGROUND OF THE INVENTION

A number of methods have been applied to study the statistical properties of genome sequences. Among the aims were the distinguishing of the coding regions, the exons, revealing of the signatures of particular features in the gene sequences, e.g. Bayesian model using Stochastic Search Variable Selection for genomic selection, statistics of consensus sequences for the most common nucleotides, Signals models, Weight Matrix Method, Markov models, multiple alignment of sequences (for given proteins), particular ways of splitting the sequences into two (phylogenetic partition). Kolmogorov-Smirnov method was among the applied ones. These and other methods inquire into various statistical features of the genome structure depending on the particular aim, which are far different from those addressed by KSP. Let us briefly outline the differences between the Kolmogorov-Smirnov test and the Kolmogorov (Kolmogorov-Arnold) stochasticity parameter (KSP) used below. The former is a long known test, while the second one has been developed by Arnold in 2008-2009. (Arnold does not even quote long known Kolmogorov-Smirnov method in his those papers.) Arnold defines KSP as an objectively measurable degree of randomness of observable events. That definition is similar that of Kolmogorov-Sinai entropy h(T) of Ergodic theory (Cornfeld, I., Fomin, S., and Sinai, Ya. G. Ergodic Theory. New York, Springer-Verlag, 1982): if h(T) >0, then a dynamical system T is chaotic (simplifying the mixing/chaotic terminological link). However, and it is crucial, that h can be used to compare quantitatively different dynamical systems. Dynamical system T_1 is said to be more chaotic than T_2 if h(T_1)>h(T_2)>0. h(T)>0 is the "Kolmogorov-Sinai test" (chaotic or not), h(T_1)>h(T_2)>0 is the "KSP test" (degree of randomness). Most importantly, KSP is applicable to even strongly correlated datasets (Arnold 2008, 2009). KSP technique has been applied to strongly correlated datasets of cosmic microwave background, considering those as not temperature 2D-maps but as 1D scalars, where the variable (temperature) is given by a random (Gaussian) field. The options are the consideration of (a) one sample from n-dimensional multivariate Gaussian distribution, or (b) n samples from (different) univariate Gaussian distributions. As for the Kolmogorov complexity (algorithmic information), it is also entirely different concept than KSP since deals with the minimal length of the coding string (computer program) for the Turing machine and hence is a unreachable quantity; see e.g. (V. G. Gurzadyan, 2005) for the complexity estimation of the human genome. Thus the Kolmogorov-Arnold technique provides novel possibilities to monitor the statistical properties of the genomic sequences, and to reveal somatic alterations.

BRIEF DESCRIPTION OF THE DRAWINGS

FIG. 2. The dependence of characteristics of the $\chi^{2'}\Delta$, vs the parameter a.

DETAILED DESCRIPTION

The invention is based on the Arnold's development of 2008-2009 (Arnold V. I., ICTP/2008/001, Trieste, 2008; Uspekhi Matemat. Nauk, 63 (2008) 5; Trans. Moscow Math. Soc. 70 (2009) 31; Funct. Anal. Other Math. 2 (2009) 139) of the work of Kolmogorov of 1933 (Kolmogorov A. N., G. Ist. Ital. Attuari, 4 (1933) 83). Consider $X_1, X_2, \ldots, X_n$ independent values of the same real-valued random variable X in growing order $X_1 < X_2 < \ldots X_n$ and let (Kolmogorov 1933; Arnold 2008)

$$F(\chi) = P\{X \leq \chi\}$$

be a cumulative distribution function (CDF) of X. The empirical distribution function $F_n(x)$ is defined as $$F_n(X) = \begin{cases} 0, & X < x_1, \\ k/n, & x_k \leq X < x_{k+1}, \\ 1, & x_n \leq X. \end{cases}$$

Kolmogorov stochasticity parameter is $$\lambda_n = \sqrt{n} \sup_x |F_n(x) - F(x)|.$$

Kolmogorov theorem (Kolmogorov 1933) states that for any continuous F $$\lim_{n\to\infty} P\{\lambda_n \le \lambda\} = \Phi(\lambda),$$

where $\Phi(0) = 0.$, $$\Phi(\lambda) = \sum_{k=-\infty}^{+\infty} (-1)^k e^{-2k^2\lambda^2}, \lambda > 0,$$

the convergence is uniform and Kolmogorov distribution $\Phi$ is independent on CDF. The reasonable values of the function $\Phi$ correspond to the interval $0.3 < \lambda\_n < 2.4$; $\lambda$ itself is a random variable with a mean $$\lambda_{mean} = \int \lambda \phi(\lambda) d\lambda \approx 0.875029$$

This technique has been applied to the study of the properties of the datasets of cosmic microwave background radiation obtained by Wilkinson Microwave Anisotropy Probe (WMAP), including e.g. the study of the so-called Cold Spot and supporting its void nature, enabling the detection of point sources (quasars, blazars) in WMAP data later discovered by Fermi satellite, for detection of galaxy clusters based on X-ray dataof XMM-Newton space telescope (V. G. Gurzadyan, A. A. Kocharyan, Kolmogorov stochasticity parameter measuring the randomness in the Cosmic Microwave Background; Astr. & Astrophys. 492 (2008) L33; V. G. Gurzadyan, A. A. Starobinsky, T. Ghahramanian, A. L. Kashin, H. Khachatryan, H. Kuloghlian, D. Vetrugno, G. Yegorian, Large Scale Plane-Mirroring in the Cosmic Microwave Background WMAP5 Maps, Astr. & Astrophys., 490 (2008) 929; V. G. Gurzadyan, A. E. Allahverdyan, T. Ghahramanyan, A. L. Kashin, H. G. Khachatryan, A. A. Kocharyan, H. Kuloghlian, S. Mirzoyan, E. Poghossian, Kolmogorov CMB Sky, Astr. & Astrophys. 497 (2009) 343; V. G. Gurzadyan, A. L. Kashin, H. G. Khachatryan, A. A. Kocharyan, E. Poghosian, D. Vetrugno, G. Yegorian, The power spectrum of the cosmic microwave background Kolmogorov maps: possible clue to correlation of voids, Astr. & Astrophys. 506 (2009) L37; V. G. Gurzadyan, A. L. Kashin, H. G. Khachatryan, A. A. Kocharyan, E. Poghosian, D. Vetrugno, G. Yegorian, Kolmogorov analysis detecting radio and Fermi gamma-ray sources in cosmic microwave background maps, Europhys. Lett. 91 (2010) 19001; V. G. Gurzadyan, A. E. Allahverdyan, T. Ghahramanyan, A. L. Kashin, H. G. Khachatryan, A. A. Kocharyan, S. Mirzoyan, E. Poghosian, D. Vetrugno, G. Yegorian A weakly random Universe? Astr. & Astrophys. 525 (2011) L7; Gurzadyan, V. G.; Durret, F.; Ghahramanyan, T.; Kashin, A. L.; Khachatryan, H. G.; Poghosian, E., Detection of X-ray galaxy clusters based on the Kolmogorov method, Europhysics Lett., 95, 69001 (2011). V. G. Gurzadyan, I. Ciufolini, S. Sargsyan, G. Yegorian, S. Mirzoyan, A. Paolozzi, Satellite probing General Relativity and its extensions and Kolmogorov analysis, Europhysics Lett. 102 (2013) 60002.)

Important class of sequences, particularly for the genomics problem, include those discussed by Arnold (quoted above papers, 2008, 2009) and represented in the form (V. G. Gurzadyan, T. Ghahramanyan, S. Sargsyan, Degree of randomness: numerical experiments for astrophysical signals, Europhys. Lett. 95 (2011) 19001)

$$z_n = \alpha \chi_n + (1-\alpha)\gamma_n,$$

where $x_n$ are random sequences and $$y_n = \frac{an(\bmod b)}{b},$$

are regular sequences, a and b are mutually fixed prime numbers; both sequences are defined within the interval (0,1) and have uniform distribution, a indicating the fraction of random and regular sequences. When doing statistic with large number of sequences, each new sequence $y_n$ is taken as the continuation of the previous one from the same arithmetical progression.

Thus one has $z_n$ with a distribution function $$F(X) = \begin{cases} 0, & X \le 0, \\ \dfrac{X^2}{2\alpha(1-\alpha)}, & 0 < X \le \alpha, \\ \dfrac{2\alpha X - \alpha^2}{2\alpha(1-\alpha)}, & \alpha < X \le 1-\alpha, \\ 1 - \dfrac{(1-X)^2}{2\alpha(1-\alpha)}, & 1-\alpha < X \le 1, \\ 1, & X > 1 \end{cases}$$

Figure 1:
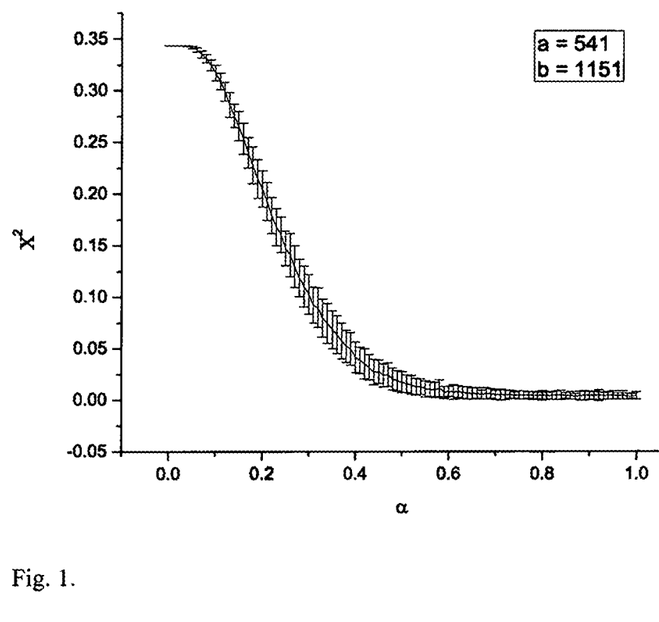
FIG. 1. The $\chi^2$ for the Kolmogorov function for the sequence $z_n$ vs $\alpha$ indicating the contribution of the random and regular parts for the pair of indicated input parameters.

Analyzing the stochastic properties of $z_n$ vs the parameter $\alpha$ varying between 0 and 1 for different values of the parameters a and b, i.e. corresponding to from purely stochastic to purely regular sequences, the FIG. 1 can be obtained. FIG. 1 shows the $\chi^2$ for the empirical distribution functions $G(\Phi)_m$ and $G_0(\Phi)=\Phi$ as indicator for randomness. Thus one parameter $\chi^2$ is calculated per each of the (100× 101) sequences. Grouping 100 $\chi^2$ values per one value of a, one can construct the mean and error values for $\chi^2$, resulting the behavior for each pair of a and b at the dependence of $\chi^2$ on $\alpha$. Thus the variation of $\chi^2$ vs $\alpha$ varying from 0 to 1 indicates the gradual change of sequences $z_n$ from regular to random.

Figure 2:
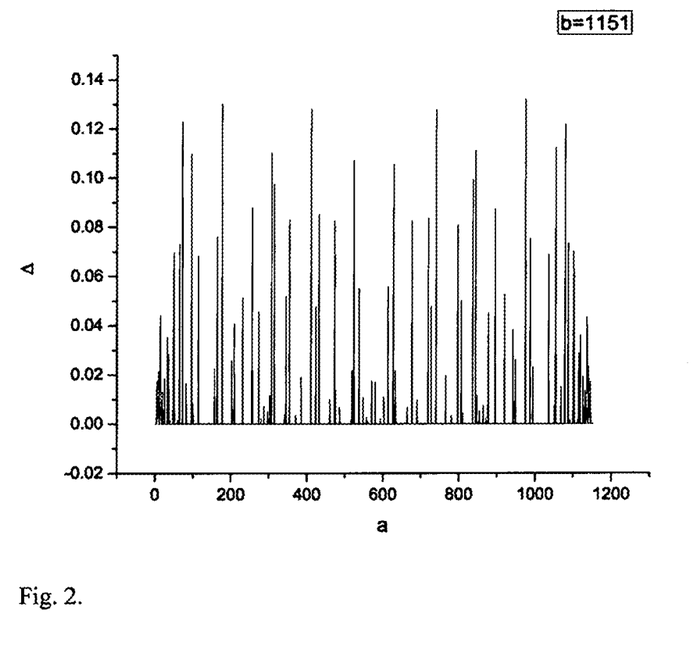

That sensitivity on the parameter a on b is defined via the parameter A which equals the difference of two values in the $\chi^2$ plots: maximal value of $\chi^2$ and minimal value in the range a from $(0, \alpha\_\{max\})$, where $\alpha\_\{max\}$ is the position of the maximal value. FIG. 2 shows the strict mirror symmetry in the dependence of $\Delta$ vs a, although no periodicity has been found by Fourier analysis.

The features of signals formed as sum of many fluctuations, each having the same standard deviation, with the $\chi^2$ frequency counts for the set of random and regular sequences as compared with a Gaussian function, also reflect the informativity of the method.

Consider a regular sequence given as $$a_i = \frac{1}{\sqrt{N}} \sum_{k=1}^{N} \text{Compact}(x_i^k, -1, 1),$$

Where $\chi^k$ is compactified arithmetical sequence within the interval $(-1,1)$, with step $1/k$, and $$b_i = \frac{1}{\sqrt{N}} \sum_{k=1}^{N} \text{Random}(-1, 1),$$

as a random one. Compact(x,p,q)=q+x mod(p−q) indicates multiples of (p−q) from x having the value within the range (p,q), p<q.

Figure 3:
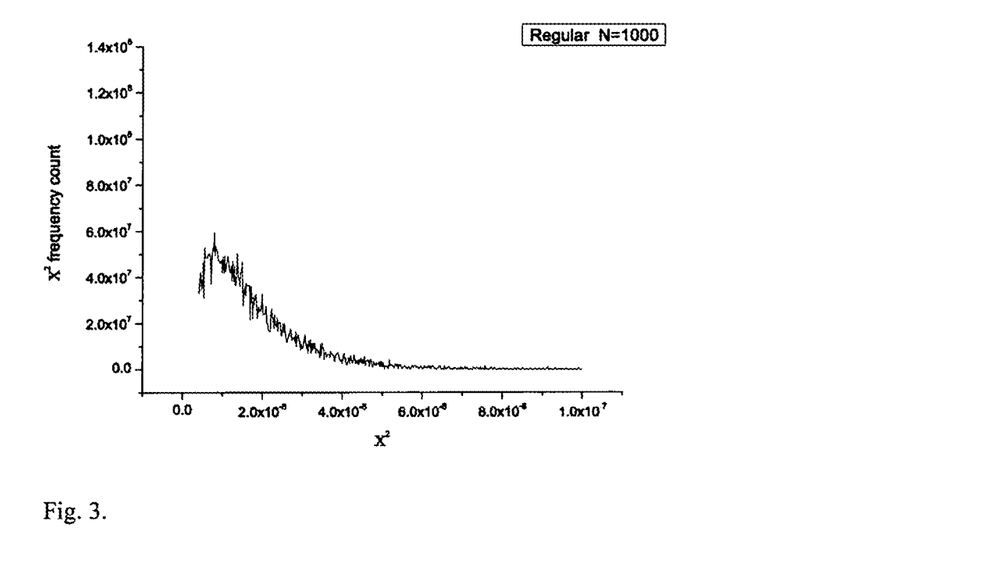
FIG. 3. $\chi^2$ frequency counts for the set of regular sequences as compared with a Gaussian function.
Figure 4:
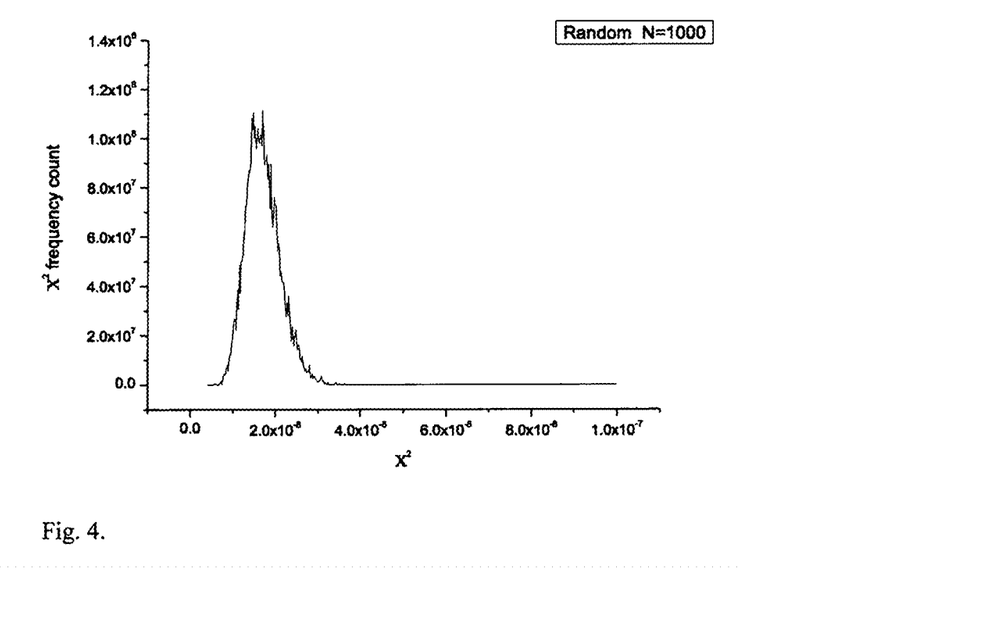
FIG. 4. The same as FIG. 3 but for a set of random sequences.

The results for 10000 random (generated by random number generator) and regular sequences each are shown in the two FIGS. 3 and 4 for $\chi^2$ with varying the number of the fluctuations.

Figure 5:
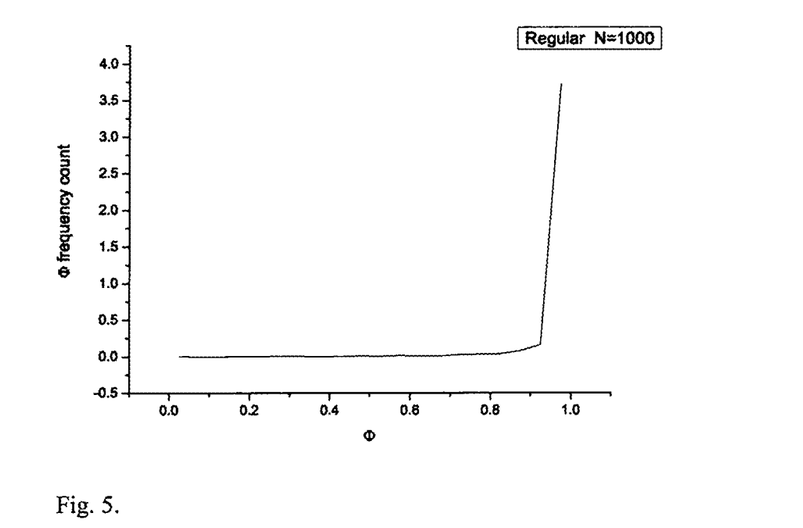
FIG. 5. Kolmogorov function $\Phi$ for the sequences in FIG. 3.
Figure 6:
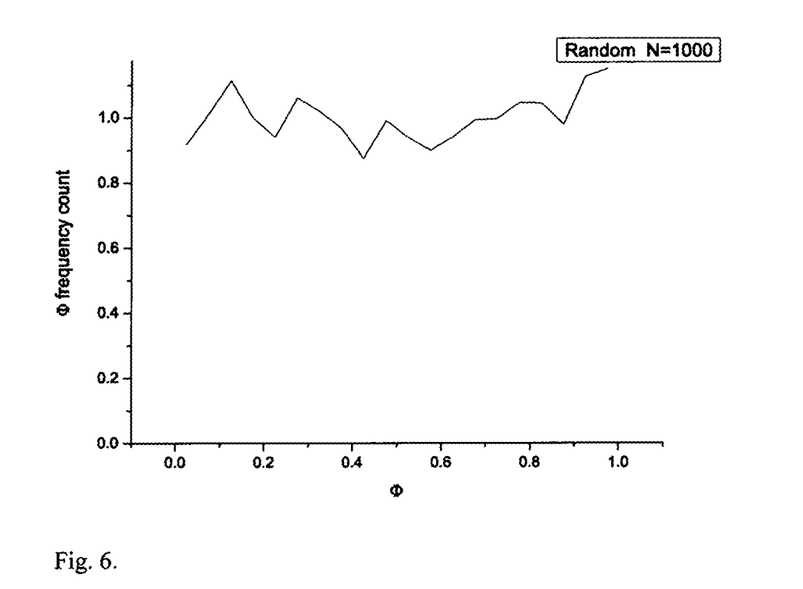
FIG. 6. Kolmogorov function $\Phi$ for the sequences in FIG. 4.

It is seen from the FIGS. 5 and 6, that although Gaussians are maintained both in random and regular cases, the behavior of Φ is radically different, thus revealing the possibilities of this method.

Figure 7:
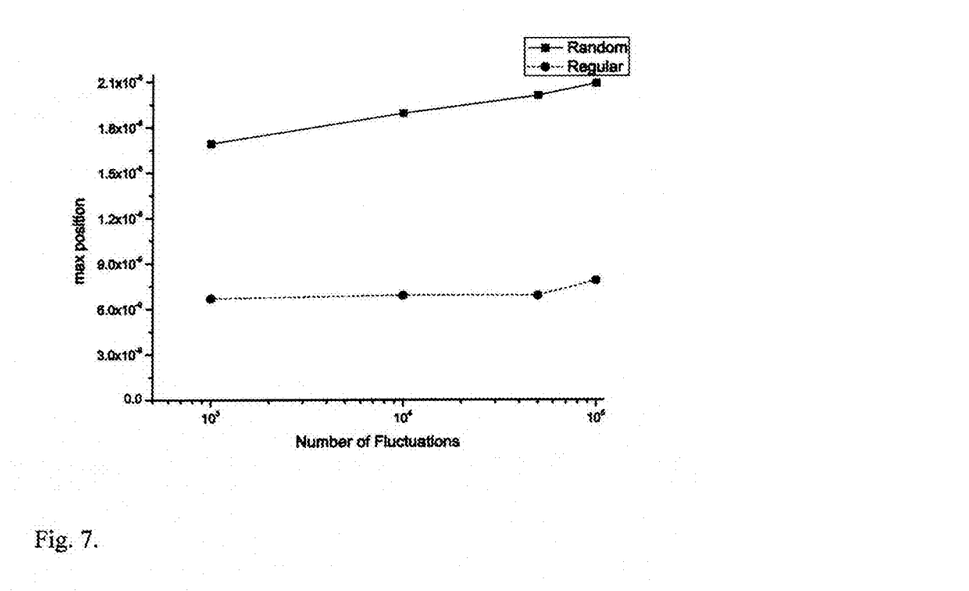
FIG. 7. The maxima of $\chi^2$ in FIGS. 5 and 6 vs the number of the fluctuations.

One more indication shown in FIG. 7 is the revealed weak dependence to the number of fluctuations.

Genomics Application.

The objective is the sequencing analysis of samples to identify tumor-specific (somatic) sequence and copy number alterations. The procedure is illustrated below via the dataset of the genomic DNA purified from tumor and normal specimens. DNA samples were enriched for coding regions in the genome using custom DNA capture approaches. Sequence data were mapped to the reference human genome sequence and sequence alterations were determined by comparison of up to 57 million 100 digit rows of G,A,T,C bases of tumor and normal DNA. The study of somatic sequence alterations has been performed via the Kolmogorov-Arnold analysis for the dataset. Input data, i.e. the sample rows, for row's position numbers 30259203 to 30259205, are shown below for Seq. ID No 18:

TATGTCCCCCAATAAACTGTAAGCTTCAGGGGGAATGAGTGAATGACCAG

TGTTCTAAGTAGAATCTTAATCTTGGATTGTTAACTCAATGAATTCTCAT

ATGTGGTCCCTGGGCTTCTCCATTCACCAGCCCCCAATCATTTCTTCCTG

TACAAGGAATGAAACAGTCATTGAGGTCACCTCTAGCAAGTCTCCCAGCA

GATAGCTACCACTTTCCACATCACAGTAGTAATAAATTAAATCATAATAT

ACTTAATATTAGGTGTACTTTTTAAAACTAAATTTTAAAAGAAAAAGGAG

The sample of 10 somatic sequence signatures have been studied for a set of data (each string of over 5000 mln nucleotides), and the presence of each somatic sequence can be summarized as follows.

| Gene Symbol | Sequence Context | N all | 81 N1 | 82 T1 | 83 T2 | 84 N2 | 84 N1 | 84 N2 | 84 T1 | 84 T2 | 121 N2 | 122 N2 | 150 T2 | 151 N2 | 151 T2 |
|---|---|---|---|---|---|---|---|---|---|---|---|---|---|---|---|
| ABP1 | GAGCCNAAGAC | 1 | | | | | | | | | 1 | | | | |
| AOX1 | AGGCCNGCCCT | 3 | 1 | | | | | | | | | | 1 | | 1 |
| APOB | GATCTNAAAAA | 2 | | | 1 | | | | | | | | | | 1 |
| ATRX | GTGAGNACGTT | 1 | | | | | | | | | | 1 | | | |
| CLASP2 | GTGACNCATAG | 1 | | | 1 | | | | | | | | | | |
| DDX27 | AAAACNTCTCG | 0 | | | | | | | | | | | | | |
| DOCK9 | TGCCTNTGGAT | 4 | | | | | 1 | | 1 | | | | 2 | | |
| hFAM131B | TCATGNCTGTG | 3 | 1 | | | | | | | | | 1 | | | 1 |
| FASTKD3 | TCAAGNTGATT | 3 | | 1 | | | 1 | | 1 | | | | | | |
| FZD7 | GACTGNGGTAT | 0 | | | | | | | | | | | | | |

The mutations listed in the above table can be located in the sequence listing as follows: GAGCCNAAGAC Seq. ID No 3, AGGCCNGCCCT Seq. ID No 4, GATCTNAAAAA Seq. ID No 5, GTGAGNACGTT Seq. ID No 6, GTGACNCATAG Seq. ID No 7, TGCCTNTGGAT Seq. ID No 8, TCATGNCTGTG Seq. ID No 9, TCAAGNTGATT Seq. ID No 10. There is no mutations AAAACNTCTCG and GACTGNGGTAT in our data sample, which is reflected in the zero values for the frequencies of these mutations.

An example of the presence of the somatic sequences in two samples of this Table is shown below. The data for the sample 084N2 are in the Seq. ID 1, and the data for the sample 151N2 are in the Seq. ID No 2.

Seq. ID No 1 for sample 084N2 and position numbers 34588855 to 34588889
ACAGAGCTGAGTCACGTGGTGGAATAAATACAAGTGTGTTGGCTCAAGCC
CAGAGTTGCTGATAGGGAGATGGATGCCTCCTGCCCCATGGGCTGTAAAC TGCCTGGAACATGACCCTCCTAGACCAACTCCACACTGGACTTCATCAGC
AACTGCAACACCTGGAGACCTGCTTGCTGCAGGTAGTGGGAGAAGGAGAA GCTCAGAGGAGTGGGAATGGGGTGGGTCTTCCTGGGCATGGCCAGGCTGT
GCCCCAGCCTAGGGGCTTGGTGTGGTGGTGTTGGCCAGGCTTGGCAGGCA TAGTAACTCTGATATGCAGTTGGGTAATTTAAAAATTGTAGTTTAAGTGG
TTTCTGCACGAATCTAGATTCTCTAAATGAAATCTAACTCAGCTCCCATA TTCCACTGCTTAAACTGAGCACAGGACGTGCACTTGGATAGTAAACCAGG
TGTCTCCTCAAAGCCCTAATATATTCAGCATCTCTATCAAAGGCGCCTTT GAGAAAGACTTAAGCATGATGCCCCCCCGCACTGACTTTCATGTGGCAGC
CAAGCAAGCGCCGGACTCCTCAAGGGCTGGCAGGAGAGCAACAGGAGATG TTCCAGCCTTGGGCATAGTCAGGGACTCTCGTGGGACCCCCCGAGTAGAA
ACACAGATGTGTCTCCCTGGGTCCCTGCCAGGTCCCCTCTCAGCCTGGAT CCATTGAAACCAATGCTATGCATACCACTCCTCCTTCCAAGGCTGTCATC
TTGCAGTCTGCCTCTGTCTCCAAGAAGTACCTCCCATTTTACCTGGGGCT CCCGAGCCTCTCCTCGTGGGGAAGGCGACACACAGCAGCCGTGAAGGTGG
CTGCCGAGAAGTTGCCCAGGCTGCTTCCAAAACCCACGGCCTGCTCCACG GTTTTGAACATTTGGCAATGTGTATTAGCACAGCTCTTCCCTTTAGCAAG
ATTTGTTTTGCGGTTCCAGATAGGTCATTTCCAGGCCTCATTCCGCCAAG NNNNNGGTTAACCAAGGAAAAAAACTTAAAAGGCATCATTGTAAACA
*TCAAGNTGATT*TGCAGAAGTTGAATNATTGATTTGAAAGTTTTAAT
TTTGTAA TTCTCTATTTTCCTAGTTATATATGCTATCATATGTCTGTTTTTCTCCTC
TTGAAGTTTCCCTGAAACCTGGGCTCTTGAAGACGCATCACTGGAGCAGA CCTCAGAGATGTTGACCCCAGCTGGGACATCAGTACCACACGCCACAAAA
TCCCCATGTCAATAGCACCACCCCTTCCCTCTGCTGGAGGATACAATCCC -continued
AGCCCCACAGAGGGATCCCTTACTACTGGAATGCAGACACAGACGTTGGA
TCCTGGTTCTCCCCAGATGACACCAACTCCGTGGTTACCAAATAGGCAAA CCCTTCCTCTGTCAGTACTGCTGTGAACAGACCTGCGTGGCTGGTCCTGT
GTTTGGGTAAAACATTAAATGACAACTTTAATTGAAAAAACCTGGGGAAG GCCAGAACACTGATTGGTGGATACCCTCGTCTTCAGTCTCTCTGGAGTCC
TTTCACTTCCATTGCCTTCGGGACAGGGAACACCTCCTCCCCCACCCTCA CCCCAGGGAGGGCAACGTTCATTCTGCTGTGGCAATGGGCCTTGGGGGAT
AGGAGTTGGATATCTGCGTAAGGGAGGACAGGTGGAAAGTGATATGGAAC GTGCGTAAAATGACAAGTCAAGGAACGACAGGAAGCAGGGAAAGTCGACA
CACTGCAAGAAAAATAGTGATAATGCTAAATAAAAAACCGTCATGAGAAA -continued CATGCACCCCAACTAAGCTCAGGTCCTGCGTAGATTTTTGTGGGAATCAG
CTTCCAAGGACTAGGTCATTTATTGGCCCTGTGTTCCTAGGTCAGCGGTG GAGGTATGGTCAACCTATAGTAAGTTAGTAAATGATAAGGGGAGGAAGAA
ATGGAAACCTAAACATCTACTGCAATGAAAACCAACAGCAATATCAGGAG AGAACAAACAAAACTATAGTGCTGGACACAAGTGGAAAGTATATTACCTT
CATTAAAATTATCTTCCTGACATGCAGTGAGGAAATTGTGTTTCCAAAGA Seq. ID No 2 for sample 151N2 and position
numbers 30259182 to 30259205
CCCAAGCTGGAATGCAGTGGCTGTTCACAGATGCAGTCATAGCACTGTAG
AGCATCAGGTGTTCCTCCCATGGCAGGAGGGAAGAAACCCAGCAAACGTC AATGAAAGTCAAATGAAATCTTTAGATGTCCTTCCATATTTTATGGTGAC
GATCTGCATCATGGGTCCGGCGGGTCCGGCCCAGGCAGCCTCTGGAGCAA AAATGGGATACAGAAAAAGACAGAACATCATAGTTCTAAGTTACTGATTT
GGAGTTTCACTCTTGTTGCTGAGACTGGAGTGCAATGACGCGATCTCGGC GACTCACTGGAGGAATGTGCCATCACTTGTTCAAATAGCCACGGCCCTTG
AGTGAAGAGGCTGGGGATGACACTACCACTGTACTGTTCTGGCATGCTCT TTTTTTCCTTTCTTTCCTTTAGAAGAAGTAGATGAACGAGACGATGCAGC
TCTGCCATTCAAGGCTCTAATGTTCCTAACCCTGATGAGGCCGTCCCTAG TGGCATCACTGAGGCACTGTACGGTCCTTGCAATGTCAAACTTACTCAAT
AGTTNTCTGATTGCTTCCCCTTCCATAGGTTGTGGGAATAATTGAGTCAC CCAAGAAGGCCTTGACCTTTCCAGCAAGTGGGAAGGTATAATCAGTCTCC
TAGAGCAGGACTCACCTGTTTTAACTCCACCTCCCGCCCCAACCCCAGTG GAGATCATTCGCATAAAGGGCCTGGGCCACTGAACGGGCTAAGCAAATAT
GAATTATTTGGATCGGTTGGCAGAAGAGGTCAATGATAAATTGCAAGAAA ACTCTACTTTGAGGACAGTCCGGCTCTCAAGGAGCACGTCTTCCACAACC
TGATCTCTCTTTCTTTACCCTACATCCAAGGGCTTGAACATTTCTTGACT GCCTTTGGGAGACCCTCTTCAGATGACTGCCATCAAAAGAGTCATAGAAA
GCTGTGCAGGGCATCCCAGACAGGGGTTGGGCCTCCCTGATGGACAAGGA CGCCTCCCTATTCCTCTNNNANCAGGTCTCAAG*GTGAGNACGTT*AAGCCT
TCCCTCACCCCCTCACAGTGGTGCAGTTCTCGGCCTCTCGGCCTGGCTTC TCTATGTATGTCACATGCACTTGCTTAACTCTAGGCATGAAGAACTTCTC
GAATGAATACAGAGTTCCTGAACTGAATGTTCAAAATGGAGTGTTAAAAT ACTTCTAATTTTTTCTAACAGGCTCCACAATCTCTCATATATGTTTTTT
TGTTATGTTGACACTGAAGTGGAAATGAAAGAAATCTATACAAGTAACCA GAGGAAGAACCTGCAGGAGCCATCCCTGACTTGCTTTGACCAAGCCCAAG
GTTTAAAAGTTTGTCCCAGACCTCCAGTTATAATGCTTCTATGGCAGATT TAGATTCTGCTGCAGTTGTTCTTCTTTTTGTATAAATAATCTTCTTTGTT
TGGGCACACCAGCTGTTGCCTTCTGGTGGGTGGGGCTGGGTGGAGCCACC TTTAGACGTTCTACATCAATAGCTCCCAATTTGAGGTACTTGGGCTGCTT
TCCTGACAGCTTGGGGTTTGAGACCCTGGAAAACTGCAGGAAGGTACCGT GATTCAGGTGCATTTGTTTCAAGCCTTGAGGTTTCATGGGGCAAATGATG
TTGAAGTTTAAGAATATCAACGTTTTATATGGTATTGTGTTTTTAGGAAC TCTCCTGTATGAGTTGTCTGATGTTGAGTAAGGCATGAACTACGGTTAAA
ATGCCCAACACCTGGCTTGCCCACCCTCCTGTCCCCTGCCCCTTCCTGGT ACACACAATTGTATAGATTGCCAGCTTTTTTATAAACTGGAAATTTCTTG
AAATCATCCTACCAAAAAGACATACATGCTCGCATGTTCACCACAATACT TATGTCCCCCAATAAACTGTAAGCTTCAGGGGGAATGAGTGAATGACCAG
TGTTCTAAGTAGAATCTTAATCTTGGATTGTTAACTCAATGAATTCTCAT ATGTGGTCCCTGGGCTTCTCCATTCACCAGCCCCCAATCATTTCTTCCTG
TACAAGGAATGAAACAGTCATTGAGGTCACCTCTAGCAAGTCTCCCAGCA GATAGCTACCACTTTCCACATCACAGTAGTAATAAATTAAATCATAATAT
ACTTAATATTAGGTGTACTTTTTAAAACTAAATTTTAAAAGAAAAAGGAG

*GTGACNCATA G*

Kolmogorov function Φ(λ) has been obtained based on the codon coding for the row (string) containing the somatic sequence (mutation) and the average for 10, 20, 50 rows without mutations distributed prior or after the rows with mutations, with varying number of digits in the rows. The histogram in FIG. 8 below shows the results for the subsequences of 100, 50 and 25 digits, i.e. nucleotides (noted as 'word').

Figure 8:
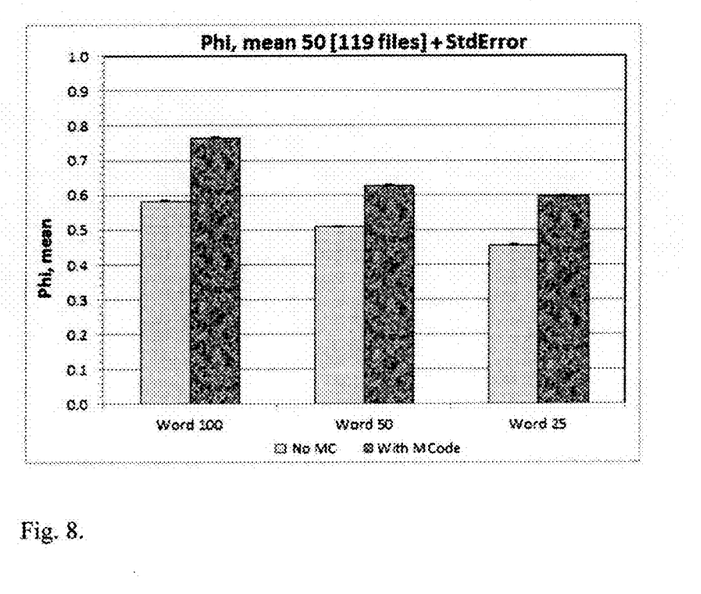
FIG. 8. The function $\Phi$ for the rows with a sample of somatic (tumor) sequences (red) and normal ones (blue) averaged over the set of somatic ones and the 20 rows, prior and after the somatic ones.
Figure 9:
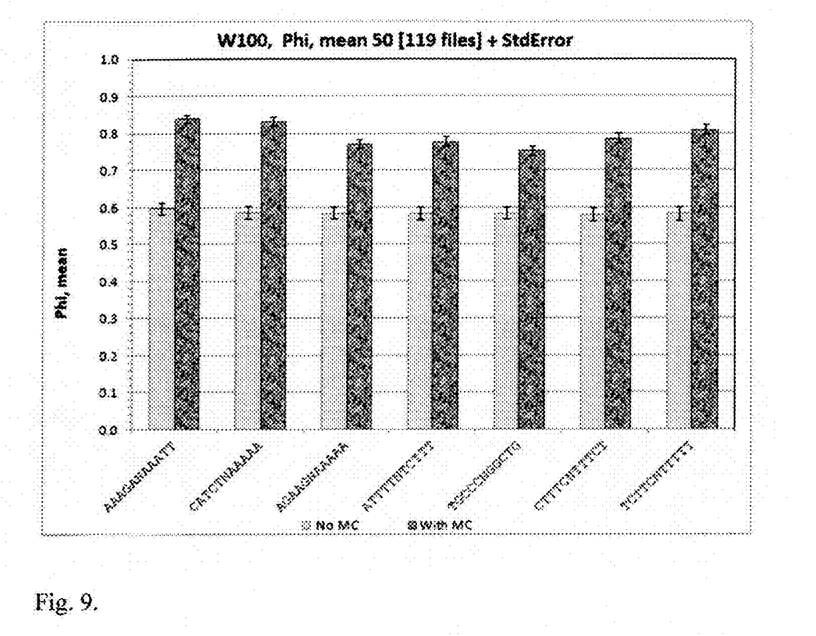
FIG. 9. The same as in FIG. 8 but for denoted somatic sequences (mutations). The mutations listed in the figure can be located in the sequence listing as follows: mutations AAAGANAAATT Seq. ID No 11, CATCTNAAAAA Seq. ID No 12, AGAAGNAAAAA Seq. ID No 13, ATTTTNTCTTT Seq. ID No 14, TGCCCNGGCTG Seq. ID No 15, CTTTCNTTTCT Seq. ID No 16, TCTTCNTTTTT Seq. ID No 17.

The function Φ reveals the difference in the coding for somatic/(tumor(indicated as with MC, black) and normal (gray) genome sequences. The averaging is for 119 files in the particular blocks of dataset with a sample of somatic sequences. The error bars, as expected, decrease for smaller sequences. FIG. 9 exhibits the Kolmogorov function for a sample of somatic sequences. The CPU time for one sequence (about $10^9$ nucleotides) was about 1 hour for i7, 2600 3.4 GHz processor of 6 GB memory.

The results of the modeling of generated systems on the one hand, and the stability of the results of the real genomic strings with respect the number of the averaged rows, namely, for row numbers e.g. 10, 20, 50, 70, and their mutual sequences on the other hand, do confirm the efficiency of the method for such strings.

This demonstrates that Kolmogorov's analysis is sensitive to genome coding differences at least for a sample of somatic/tumor specific vs normal sequences, and thus can act as a tool for detection and study of corresponding genome coding properties.

Our approach differs from those using the Kolmogorov-Smirnov test, such as in U.S. Pat. No. 8,560,469 B2 (2013), U.S. Pat. No. 7,809,765 B2 (2010), U.S. Pat. No. 6,291,182 B1 (2001), since we deal with the stochasticity parameter as degree of randomness as defined by Arnold (2008, 2009), the theoretical and empirical codon coded distributions, and obtain semi-robust quantitative characteristics for the mutation and normal (without mutation) genomic sequences.

The invention claimed is:

1. A method to identify a mutation in a sequence isolated from a subject comprising the steps of:
   isolate a nucleic acid from a genome of a subject;
   sequence the nucleic acid from a subject to obtain nucleic acid sequence data of the genome of the subject;
   provide nucleic acid sequence data of the genome of the subject;
   obtaining the frequency counts for each combination of a 3-base combination of nucleotides wherein the obtaining is performed by starting from the first nucleotide, from the second nucleotide, and then from the third nucleotide in the sequence of a subject;
   constructing a theoretical cumulative distribution function (CDF) from the frequency counts for each 3-base combination present in the nucleic acid sequence data of the genome;
   determine an empirical CDF from the frequency counts for each 3-base combination present in a string of a sequence from the genome in the nucleic acid sequence data;
   perform a Kolmogorov-Arnold analysis between the theoretical CDF and the empirical CDF to obtain a stochastic probabilistic parameter on a computer;
   calculating a Kolmogorov-Arnold distribution function on a computer, wherein the Kolmogorov-Arnold distribution function value represents the degree of randomness, wherein the deviation from the average stochastic probabilistic parameter value of 3 sigma deviation or more from average indicates that there is a mutation in the sequence of the subject;
   determining whether the analyzed nucleic acid sequence from the subject contains a mutation.

2. The method of claim 1 wherein the nucleic acid sequence data of a test sequence is of a length of 25, 50, 1000, 300, 500 or 20000.

3. The method of claim 1, wherein said the method is applied to aligned genomic sequences.

4. The method of claim 1, wherein the method is applied to non-aligned genomic sequences.

5. The method of claim 3 or 4, wherein the method quantitatively detects at least certain somatic sequences in the dataset of the genomic DNA purified from tumor and normal specimens, based on the difference in the value of the Kolmogorov function for strings with mutations (somatic sequences) and without mutations (normal sequences).

6. The method of claim 3 or 4, wherein the behavior (values) of the Kolmogorov function for generated somatic sequences enables to distinguish between somatic sequences themselves via this method using larger datasets.

7. The method of claim 6, wherein the method determines the dynamics of the somatic sequences, i.e. disappearance and appearance of new sequences during the clinical studies.

8. The method of claim 6, wherein the method detects unknown types of mutations in comparison with normal string correlations.

9. The method of claim 6, wherein the method correlates Kolmogorov function with properties of diseases.

10. The method of claims 5 or 6, wherein it is implemented on a computer in the successive steps for obtaining the numerical value of the codon based distribution function for each combination of a 3-base combination of nucleotides, the search and localization of the mutation sequences for the given sample, the estimation of the value of the stochasticity parameter and the Kolmogorov function for the strings with mutations and for a given number of strings without mutations, and obtaining this for a given length of the string and the number of averaged strings.

* * * * *